United States Patent [19]

Wolf et al.

[11] Patent Number: 5,101,061
[45] Date of Patent: Mar. 31, 1992

[54] NOVEL BENZONITRILES, BENZALDEHYDES AND BENZYL ALCOHOLS

[75] Inventors: Bernd Wolf, Mutterstadt; Hans Theobald, Limburgerhof; Norbert Goetz, Worms, all of Fed. Rep. of Germany

[73] Assignee: BASF Aktiengesellschaft, Ludwigshafen, Fed. Rep. of Germany

[21] Appl. No.: 520,459

[22] Filed: May 8, 1990

Related U.S. Application Data

[62] Division of Ser. No. 365,794, Jun. 14, 1989, Pat. No. 4,950,796.

Foreign Application Priority Data

Jun. 21, 1988 [DE] Fed. Rep. of Germany ....... 3820896

[51] Int. Cl.$^5$ .............................. C07C 255/50
[52] U.S. Cl. ................................... 558/411
[58] Field of Search ............... 558/411, 425

[56] References Cited

U.S. PATENT DOCUMENTS 3,399,243 8/1968 Boswell .................... 558/411 X
4,570,011 2/1986 So ............................. 558/411 X

FOREIGN PATENT DOCUMENTS 862863 3/1961 United Kingdom ............. 558/425

*Primary Examiner*—Joseph Paul Brust
*Attorney, Agent, or Firm*—Oblon, Spivak, McClelland, Maier & Neustadt

[57] ABSTRACT

Novel benzonitriles, benzaldehydes and benzyl alcohols of the formula I

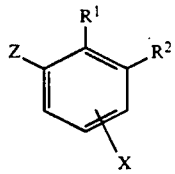

where $R^1$ is methyl or ethyl, $R^2$ is alkyl, alkenyl, cycloalkyl, cycloalkenyl, bicycloalkyl, bicycloalkenyl, or $C_1$-$C_5$-alkyl-substituted cycloalkyl, cycloalkenyl, bicycloalkyl or bicycloalkenyl, X is hydrogen, chlorine or fluorine and Z is —CN, CHO or

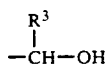

where $R^3$ is hydrogen, cyano, $C_2$-$C_4$-alkynyl, $C_2$-$C_4$-alkenyl or $C_1$-$C_4$-alkyl, with the proviso that $R^2$ is not —CH$_2$-CH=CH—B when B is hydrogen, alkyl or alkenyl and at the same time $R^1$ is methyl and Z is

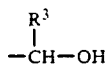

and with the proviso that $R^2$ is not methyl or ethyl when $R^1$ is methyl and at the same time Z is

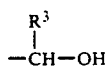

and further more with the proviso that $R^2$ is not methyl when $R^1$ is methyl or ethyl and at the same time Z is —CN or —CHO.

14 Claims, No Drawings

NOVEL BENZONITRILES, BENZALDEHYDES AND BENZYL ALCOHOLS

This is a division of application Ser. No. 07/365,794, filed on June 14, 1989, now U.S. Pat. No. 4,950,796, issued Aug. 21, 1990.

The present invention relates to novel benzonitriles, benzaldehydes and benzyl alcohols of the general formula I

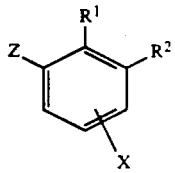

where $R^1$ is methyl or ethyl, $R^2$ is alkyl, alkenyl, cycloalkyl, cycloalkenyl, bicycloalkyl, bicycloalkenyl or $C_1$-$C_5$-alkyl-substituted cycloalkyl, cycloalkenyl, bicycloalkyl or bicycloalkenyl, X is hydrogen, chlorine or fluorine and Z is —CN, CHO or

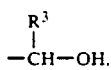

where $R^3$ is hydrogen, cyano, $C_2$-$C_4$-alkynyl, $C_2$-$C_4$-alkenyl or $C_1$-$C_4$-alkyl, with the proviso that $R^2$ is not —CH$_2$—CH=CH—B when B is hydrogen, alkyl or alkenyl and at the same time $R^1$ is methyl and Z is

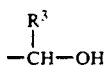

and with the proviso that $R^2$ is not methyl or ethyl when $R^1$ is methyl and at the same time Z is

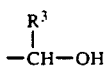

and furthermore with the proviso that $R^2$ is not methyl when $R^1$ is methyl or ethyl and at the same time Z is —CN or —CHO.

2,3-Dimethylbenzyl alcohol, 3-ethyl-2-methylbenzyl alcohol and 2,3-dimethyl-α-methylbenzyl alcohol are described in, for example, J. Chem. Soc., Perkin Trans. 1 (12) (1981), 3087-3091; J. Chem. Soc., Perkin Trans. 1 (20) (1974), 2339-2342; Helv. Chim. Acta, 60 (5) 1758-1780 and Tetrahedron Lett. 22 (1981), 161-162.

Furthermore, Pestic. Sci. 17 (6) (1986), 691-700 discloses certain ortho-methylbenzyl alcohols which carry in the meta-position an allyl radical which may be substituted at the terminal position.

2,3-Dimethylbenzaldehyde and 2-ethyl-3-methylbenzaldehyde are described in J. Chem. Soc., Perkin Trans. 1 (1981), 3087-3091, J. Org. Chem. 47 (1982), 1361-1364 and Indian J. Chem. Sect. B, 258 (1986), 1112-1117.

2,3-Dimethylbenzonitrile, 2-ethyl-3-methylbenzonitrile and 4-chloro-2,3-dimethylbenzonitrile are disclosed in J. Chem. Soc., Perkin Trans. 2 (1983), 1003-1010, Indian J. Chem. Sect. B, 25B (1986), 1112-1117 and J. Chem. Soc., 1964, 2258-2261.

It is an object of the present invention to provide novel intermediates for the preparation of pesticides, in particular of benzyl esters of the structure IV

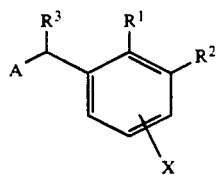

where A is a carboxylate radical of an acid component typical for pyrethroids and $R^1$ to $R^3$ and X have the above-mentioned meanings.

We have found that this object is achieved and that the compounds defined at the outset are particularly suitable for the preparation of benzyl esters IV which have good insecticidal and acaricidal activity and are described in contemporaneous German Application P 38 20 896.2.

The benzyl esters of the formula IV can be obtained by reacting an acid A—H, some typical examples of which are listed below, or a derivative of this acid, such as an acyl chloride, an anhydride or the like, with a benzyl alcohol of the general formula Ia or a derivative thereof in accordance with the equation below.

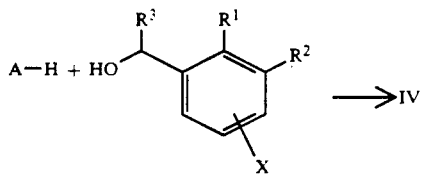

$R^1$ to $R^3$ and X have the abovementioned meanings. Typical examples of the acids of the formula A—H are:

$A^1$—H: 3-(2',2'-dimethylvinyl)-2,2-dimethylcyclopropane-2-carboxylic acid $A^2$—H: 3-(2',2'-dichlorovinyl)-2,2-dimethylcyclopropane-1-carboxylic acid $A^3$—H: 3-(2'-chloro-3',3',3'-trifluoroprop-1-enyl)-2,2-dimethylcyclopropane-1-carboxylic acid $A^4$—H: 3-(2',2'-dibromovinyl)-2,2-dimethylcyclopropane-1-carboxylic acid $A^5$—H: 3-(2',2'-difluorovinyl)-2,2-dimethylcyclopropane-1-carboxylic acid $A^6$—H: 3-(2'-fluoro-3',3',3'-trifluoroprop-1'-enyl)-2,2-dimethylcyclopropane-1-carboxylic acid $A^7$—H: 3-(2',2'-bistrifluoromethylvinyl)-2,2-dimethylcyclopropane-1-carboxylic acid $A^8$—H: 2-(4'-chlorophenyl)-3-methylbutyric acid $A^9$—H: 2-(4'-fluorophenyl)-3-methylbutyric acid $A^{10}$—H: 2-(4'-difluoromethoxyphenyl)-3-methylbutyric acid $A^{11}$—H: 3-(4'-tert-butylphenyl)-2,2-dimethylcyclopropane-1-carboxylic acid $A^{12}$—H: 2,2,3,3-tetramethylcyclopropane-1-carboxylic acid $A^{13}$—H: 1-(4'-chlorophenyl)-cyclopropane-1-carboxylic acid $A^{14}$—H: 1-(4'-ethoxyphenyl)-2,2-dichlorocyclopropane-1-carboxylic acid $A^{15}$—H: 3-[2'-(4H$_2$-chlorophenyl)-2'-chlorovinyl]-2,2-dimethylcyclopropane-1-carboxylic acid $A^{16}$—H: 3-(1',3'-butadienyl)-2,2-dimethylcyclopropane-1-carboxylic acid $A^{17}$—H: 3-(2'-methyl-2'-methoxycarbonylvinyl)-2,2-dimethylcyclopropane-1-carboxylic acid $A^{18}$—H: 2-(2'-chloro-4'-trifluoromethylphenylamino)-3-methylbutyric acid $A^{19}$—H: 2-(2'-fluoro-4'-trifluoromethylphenylamino)-3-methylbutyric acid $A^{20}$—H: 3-methyl-2-(4'-trifluoromethylphenylamino)-butyric acid $A^{21}$—H: 2-methyl-2-(pyrrol-1'-yl)-butyric acid $A^{22}$—H: 3-methyl-2-(3'-methylpyrrol-1'-yl)-butyric acid $A^{23}$—H: 2-(3',4'-dimethylpyrrol-1'-yl)-methylbutyric acid $A^{24}$—H: 2-(2',5'-dimethylpyrrol-1'-yl)-methylbutyric acid $A^{25}$—H: 2-(isoindoline-2-yl)-3-methylbutyric acid $A^{26}$—H: 1,1-dimethyl-2,2[H]indenespirocyclopropane-3-carboxylic acid $A^{27}$—H: 3-cyclopentylidenemethyl-2,2-dimethylcyclopropane-1-carboxylic acid $A^{28}$—H: 3-(1',2'-dibromo-2',2'-dichloroethyl)-2,2-dimethylcyclopropane-1-carboxylic acid $A^{29}$—H: 3-methyl-2-(pyrazol-1'-yl)-butyric acid $A^{30}$—H: 3-methyl-2-(imidazol-1'-yl)-butyric acid The reaction can be accelerated in a conventional manner by adding a catalyst, such as sulfuric acid, a hydrogen halide, a sulfonic acid or an acidic ion exchanger and the equilibrium of the esterification can be shifted in the desired direction by removing the water or the ester IV from the reaction mixture, for example by azeotropic distillation or by binding the water to sulfuric acid or a hydrohalic acid.

The corresponding acyl chlorides can also be reacted with the alcohols of the formula Ia in the presence of an acid acceptor (cf. Houben-Weyl, Methoden der organischen Chemie, Volume VIII, page 541 et seq., Georg-Thieme-Verlag, Stuttgart 1952).

Suitable acid acceptors are the conventional basic agents, in particular aliphatic, aromatic and heterocyclic amines, e.g. triethylamine, dimethylamine, piperidine, dimethylaniline, dimethylbenzylamine, pyridine and 2-picoline.

The reaction can be carried out in a solvent or diluent. The stated acid acceptors themselves or, for example, the following solvents or diluents or mixtures thereof are suitable for this purpose:

Aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene; ethers, such as diethyl and di-n-butyl ether, methyl tert-butyl ether, tetrahydrofuran and dioxane; ketones, for example acetone, methyl ethyl ketone and methyl isopropyl ketone; and nitriles, such as acetonitrile and propionitrile.

The starting materials are usually produced in a stoichiometric ratio. However, an excess of one or other of the starting materials may be quite advantageous in specific cases.

The reaction usually takes place at a sufficient rate at above 0° C. Since it is generally exothermic, it may be advantageous to provide a means of cooling.

In some cases, it is useful and advantageous to esterify the compounds of the formula Ia in situ, particularly when $R^3$ in the general formula Ia is a cyano group.

The novel esters may furthermore be prepared by virtually any known method of ester synthesis, for example by reacting the corresponding anhydride with an alcohol of the formula Ia, reacting the corresponding salt with a derivative of an alcohol of the formula Ia or by transesterification (cf. Houben-Weyl, loc. cit., pages 508–628).

In the present invention, the terms have the following meanings, unless stated otherwise:

Alkyl is straight-chain or branched alkyl of 1 to 20, in particular 1 to 12, carbon atoms. Examples are methyl, ethyl, propyl, isopropyl, n-butyl, isobutyl, sec-butyl and tert-butyl.

Alkenyl is a straight-chain or branched, ethylenically unsaturated hydrocarbon group having 2 to 20, in particular 2 to 12, carbon atoms and 1 to 10, in particular 1 to 5, ethylenic bonds. Examples are vinyl, isopropenyl, 1-butenyl, 1,5-hexadienyl, 1-methylpropenyl and 1-ethylvinyl.

Cycloalkyl is a cycloalkyl group having 3 to 8, in particular 3 to 6, carbon atoms in the ring, such as cyclopropyl, cyclobutyl, cyclopentyl or cyclohexyl. This cycloalkyl group is unsubstituted or substituted by one or more, for example 1 to 4, branched or straight-chain $C_1$–$C_5$-alkyl radicals, such as methyl, ethyl, propyl, isopropyl, butyl, sec-butyl, tert-butyl or pentyl. Examples are 3,5-diethylcyclohexyl and tetramethylcyclopropyl.

Cycloalkenyl is a cycloalkenyl group having 3 to 8, in particular 3 to 6, carbon atoms in the ring, such as cyclopropenyl, cyclobutenyl, cyclopentenyl, cyclopentadienyl or cyclohexadienyl. This cycloalkenyl group is unsubstituted or substituted by one or more, for example 1 to 4, branched or straight-chain $C_1$–$C_5$-alkyl radicals, such as methyl, ethyl, propyl, isopropyl, butyl, sec-butyl, tert-butyl or pentyl. Examples are 1-cyclopentenyl, 1-cyclohexenyl, 3,5-dimethyl-1-cyclohexenyl and 1,3-cyclohexadienyl.

Bicycloalkyl is a bicycloalkyl radical having 5 to 12, in particular 6 to 8, carbon atoms in the bicyclic structure, e.g. 2-norbornyl or bicyclo[4.1.0]hept-1-yl. This bicyclic structure is unsubstituted or substituted by one or more, for example 1 or 2, branched or straight-chain alkyl radicals, such as methyl, ethyl, propyl, isopropyl, butyl, sec-butyl or pentyl. An example is 2,6-dimethylbicyclo[4.1.0]hept-1-yl.

Bicycloalkenyl is an unsaturated bicycloalkyl group having 5 to 12, in particular 6 to 8, carbon atoms in the bicyclic structure and one or more, for example 1 or 2, ethylenic double bonds, e.g. norbornen-2-yl or norbornadien-2-yl. This bicycloalkenyl group is unsubstituted or substituted by one or more, for example 1 to 3, branched or straight-chain $C_1$–$C_5$-alkyl radicals, such as methyl, ethyl, propyl, isopropyl, butyl, sec-butyl or pentyl. An example is 7,7-dimethylbicyclo[4.1.0]hept-2-en-1-yl.

$R^3$ is hydrogen, cyano, $C_2$–$C_4$-alkynyl, such as ethynyl, propyn-1-yl, propyn-2-yl or butynyl $C_2$–$C_4$-alkenyl, such as vinyl, allyl or butenyl, or $C_1$–$C_4$-alkyl, such as methyl, ethyl, propyl, isopropyl or butyl.

In the compounds I, $R^1$ is preferably methyl, $R^2$ is preferably a branched alkyl or alkenyl radical of 3 to 8 carbon atoms, such as isopropyl, isopropenyl, sec-butyl, 1-buten-2-yl, 1-methyl-1-propenyl, 1,3-butadienyl, isopentyl, sec-pentyl, 3-penten-3-yl, 1-penten-2-yl or sec-hexyl, the three first-mentioned radicals being particularly preferred, $C_3$–$C_8$-cycloalkyl or cycloalkenyl, such as cyclopentyl, 1-cyclopentenyl, cyclohexyl, 1-cyclohexenyl or cyclopropenyl, or $C_6$–$C_8$-bicycloalkyl or bicycloalkenyl, such as 2-norbornyl, 2-nornbornen- 2-yl or 2,5-norbornadien-2-yl, $R^3$ is hydrogen, ethynyl or cyano and X is hydrogen or fluorine.

The novel compounds are prepared by the following processes:

Benzyl alcohols of the general formula Ia

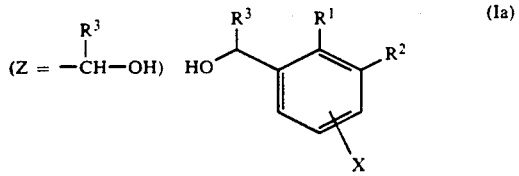

are obtained starting from a correspondingly substituted benzaldehyde of the formula Ib

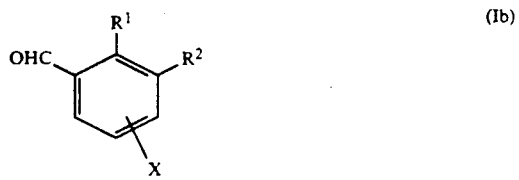

by reacting it with:
i) a reducing agent if $R^3$ is H,
ii) hydrocyanic acid or a metal cyanide in the presence or absence of an acid if $R^3$ is CN or
iii) a metalorganyl $MeR^3$ or $R^3MeHal$ if $R^3$ is $C_2-C_4$-alkynyl, $C_2-C_4$-alkenyl or $C_1-C_4$-alkyl, Me being an alkali metal, alkaline earth metal or transition metal and Hal being halogen.

Suitable reducing agents are all conventional reducing agents which convert benzaldehydes into benzyl alcohols (Houben-Weyl, Methoden der organischem Chemie, Volume VI/1b, pages 1-500, 1984 Edition, Georg Thieme Verlag, Stuttgart). In addition to the catalytic hydrogenation, nonmetallic reducing agents and metal hydrides, in particular complex metal hydrides, e.g. lithium aluminum hydride or sodium borohydride are suitable. Cathodic and photochemical reduction are also suitable.

For the preparation of the cyanohydrins, the benzaldehydes are reacted with hydrocyanic acid, with hydrocyanic acid produced in situ from metal cyanides, or with metal cyanides in the presence of an alkali metal bisulfite solution, if necessary basic catalysts, such as potassium carbonate, or phase transfer catalysts, e.g. benzyltriethylammonium chloride, being added.

Preferably used metal cyanides are alkali metal cyanides, e.g. sodium cyanide or potassium cyanide.

The reaction is carried out in a conventional manner, for example as described in Houben-Weyl, Methoden der organischen Chemie, Volume VIII, pages 274-278, 1952 Edition, and Volume E5, page 1413 et seq., 1985 Edition.

Suitable metalorganyls are the corresponding organometallic compounds, in particular lithiumorganyl compounds $LiR^3$, such as methyllithium, ethyllithium or butyllithium or the corresponding Grignard compounds $R^3MgHal$, where Hal is chlorine, bromine or iodine, e.g. methylmagnesium bromide, ethylmagnesium chloride, propylmagnesium iodide or vinylmagnesium iodide.

The reaction of the metalorganyls can be carried out in a conventional manner, for example as described in Houben-Weyl, Methoden der organischen Chemie, Volume 13/2a, page 285 et seq., 1973, in an inert organic solvent such as ether or tetrahydrofuran, under a protective gas, so that no further information is required in this context.

The benzaldehydes Ib are prepared by reacting a correspondingly substituted benzonitrile Ic

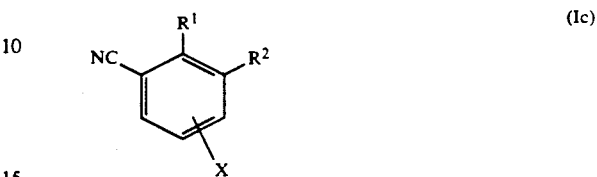

with a reducing agent to give an aldimine II

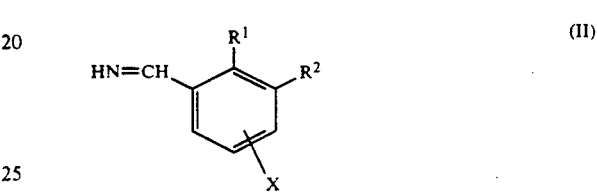

and hydrolyzing this in a conventional manner.

This reaction sequence is shown in the following equation:

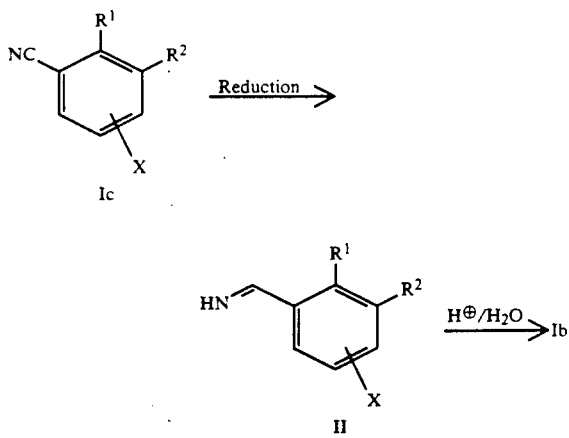

In addition to hydrogen (catalytic hydrogenation) reducing agents are aluminum hydrides, e.g. diisopropylaluminum hydride (cf. Houben-Weyl, Methoden der organischen Chemie, Volume E3, pages 476-488, Georg Thieme Verlag, Stuttgart). The hydrolysis of the aldimines II is carried out as a rule by treatment with a dilute or concentrated mineral acid, such as hydrochloric acid. In the case of sensitive aldehydes, it is advisable to use buffered acetic acid.

It is not absolutely essential to isolate the aldimines II. They can advantageously be hydrolyzed immediately to the benzaldehydes Ib, without working up and purification.

The benzonitriles of the general formula Ic are prepared by reacting

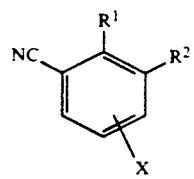

compounds of the general formula III

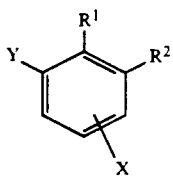

where Y is chlorine or bromine, with metal cyanides in an organic solvent in accordance with the following equation.

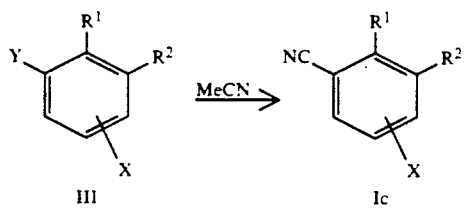

Suitable metal cyanides (MeCN) are alkali metal, alkaline earth metal and heavy metal cyanides (Houben-Weyl, Methoden der organischen Chemie, Volume E5, pages 1447–1467, 1985 Edition, Georg Thieme Verlag, Stuttgart). The use of copper(I) cyanide is particularly advantageous. The reaction takes place smoothly in aprotic, polar solvents. Dimethylformamide, pyridine, 1-methyl-2-pyrrolidone and phosphoric acid tris-(dimethylamide) are particularly suitable.

The reaction is advantageously carried out at from 100° to 250° C. When copper(I) cyanide is used, the reaction mixture is worked up (destruction of the initially formed nitrile/copper halide/copper cyanide complex) with iron(III) chloride/hydrochloric acid, 1,2-diaminoethane or sodium cyanide. 1,2-Diaminoethane is advantageously used.

Specific examples of the compounds III, such as 2-chloro-6-n-butyltoluene, 3-chloro-2-methylstyrene, 1-chloro-2-methyl-3-(1'-propenyl)-benzene, 2,3-dimethylchlorobenzene, 2,3-dimethylbromobenzene, 4-fluoro-2,3-dimethylbromobenzene, 1,2-dichloro-3,4-dimethylbenzene, 1,5-dichloro-2,3-dimethylbenzene and 1,4-dichloro-2,3-dimethylbenzene are disclosed in U.S. Pat. No. 4,538,003; European Patent 80 359; J. Med. Chem. 28 (10), 1436–1440; J. Chromatogr. 370 (3) (1986), 355–376; Gazz. Chim. Hal., 103 (8–9) (1973), 1019–1025 or Chem.-Ztg. 103 (1) (1979), 1–7.

A general synthesis route for the preparation of the compounds of the formula III where $R^1$, $R^2$, X and Y have the abovementioned meanings starts from dichloro-, dibromo-, dibromochloro-, dibromofluoro- or dichlorofluorobenzene derivatives Va and is illustrated by the following reaction scheme:

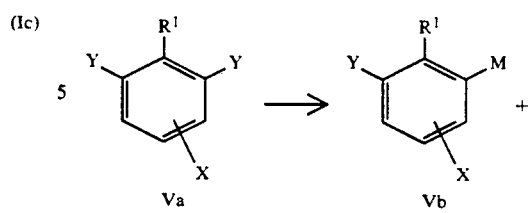

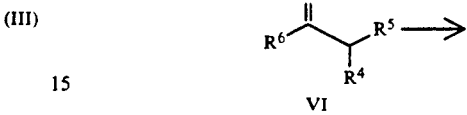

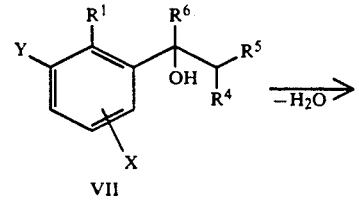

In this reaction scheme, the side chains

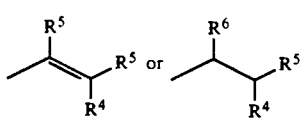

correspond to the radical $R^2$. $R^4$, $R^5$ and $R^6$ are each hydrogen, branched or straight-chain alkyl or branched or straight-chain alkenyl. $R^4$ and $R^6$ or $R^5$ and $R^6$ may furthermore be bonded to form a ring, which may be substituted by $C_1$–$C_5$-alkyl, or $R^4$, $R^5$ and $R^6$ are such that they form a bicyclic ketone, which may be substituted by $C_1$–$C_5$-alkyl.

Di- or trihalobenzenes of the general formula Va, where $R^1$ is methyl or ethyl, X is hydrogen, chlorine or fluorine and Y is chlorine or bromine, are converted into the monometalorganyls of the general formula Vb (organolithium compound or Grignard compound), where X, Y and $R^1$ have the meaning stated for Va and M is lithium or MgY.

The conventional preparation processes which start from aryl halides (cf. Houben-Weyl, Methoden der organischen Chemie, Volume XIII/1, page 134 et seq., 1970 Edition, and Volume XIII/2a, page 54 et seq., 1973 Edition, Georg Thieme Verlag, Stuttgart) are suitable for the preparation of organolithium or Grignard compounds. Where Y is chlorine and X is hydrogen, the synthesis of the Grignard compounds requires higher reaction temperatures. The use of tetrahydrofuran at boiling point has proven particularly useful.

The organometallic compounds Vb are reacted with carbonyl compounds VI, in which $R^4$ to $R^6$ have the above-mentioned meanings, to give benzyl alcohols VII. These are dehydrated to styrenes of the general formula III', the methods described in Houben-Weyl (Methoden der organischen Chemie, Volume V/lb, page 45 et seq., 1972 Edition, Georg-Thieme-Verlag, Stuttgart) being suitable. It is advantageous to use acidic dehydrating agents, in particular oxalic acid or p-toluenesulfonic acid, with simultaneous removal of the resulting water by means of a separator.

The styrene derivatives III' prepared in the manner described above are either used directly for the preparation of the benzonitriles of the general formula Ic or first converted into compounds of the general formula III'' by reduction. This may be effected both by noncatalytic reduction (for example with ethanol and sodium) and by catalytic hydrogenation (cf. Houben-Weyl, Methoden der organischen Chemie, Volume V/la, page 405 et seq., 1970 Edition, Georg Thieme Verlag, Stuttgart). Examples of suitable catalysts are $PtO_2$, Raney nickel, Pd/carbon, Pd/CaCO$_3$, copper chromite or Pd/Al$_2$O$_3$. The use of Pd/carbon has proven particularly useful. Suitable solvents are alcohols, e.g. methanol, ethanol or isopropanol, ethers, e.g. tetrahydrofuran or dioxane, and esters, e.g. ethyl acetate. It is advantageous to use ethanol. The catalytic hydrogenation is carried out, as a rule, at room temperature and under from 1 to 150 bar. Small amounts of compounds in which halogen/hydrogen exchange has additionally taken place are often formed as byproducts.

Compounds of the general formula III

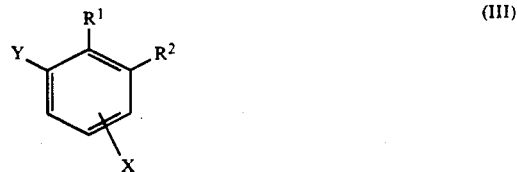

where $R^2$ is a tertiary alkyl radical or tertiary alkenyl radical, can be prepared starting from compounds of the general formula Va.

The following reaction scheme is intended as an example of the synthesis route:

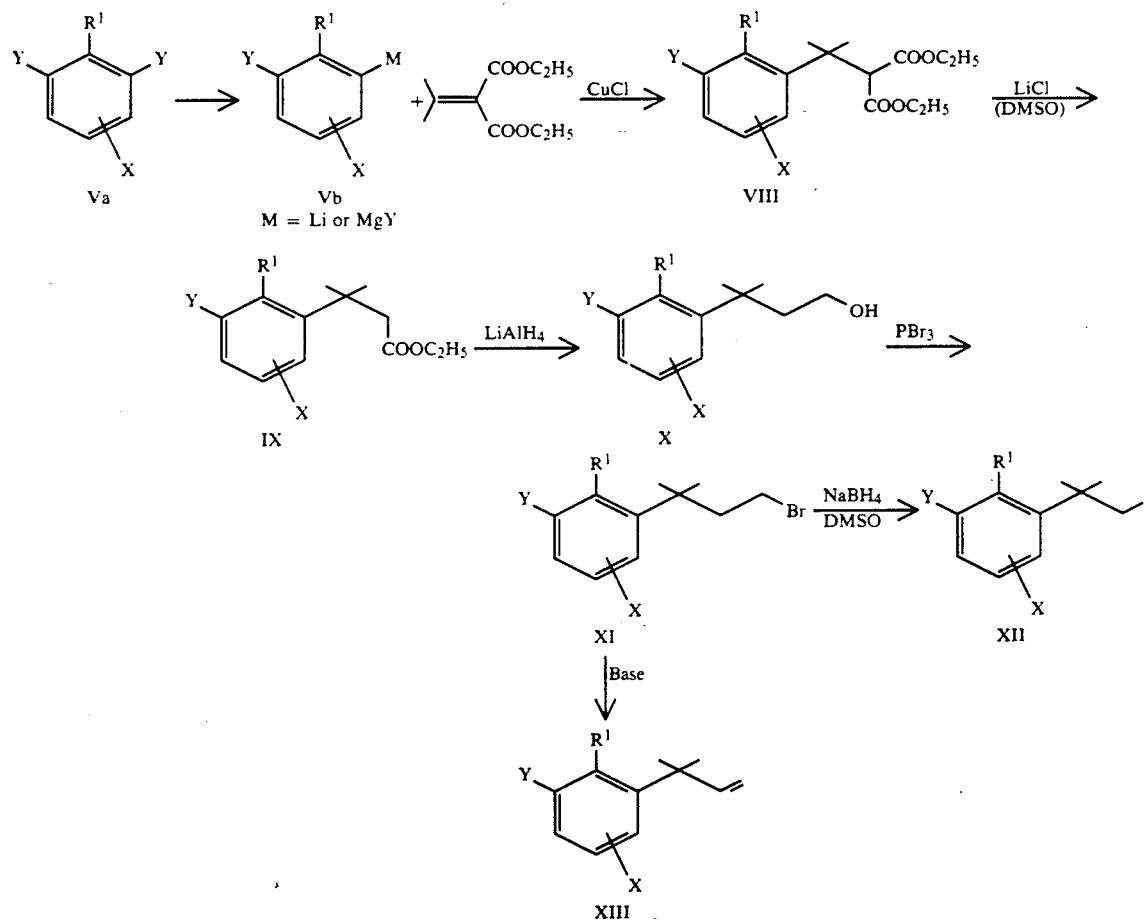

Compounds of the general formula I

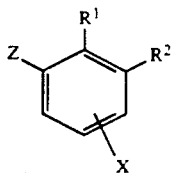 (I)

where R² is unsubstituted or substituted cyclopropyl, can be obtained by various methods:

a) By the process described below, in which the required starting materials XV can be obtained by an addition reaction of a dihalocarbene with compounds of the general formula III' followed by dehalogenation (for example with tri-n-butyltin hydride).

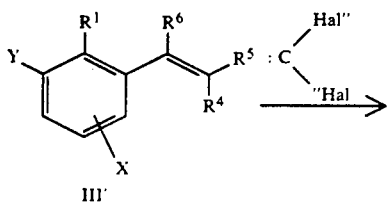

III'

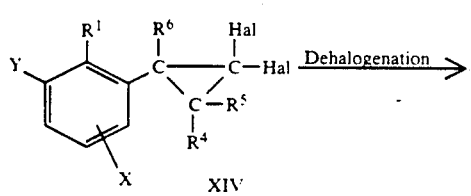

XIV

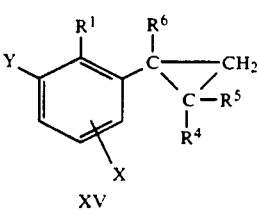

XV (R⁴, R⁵ and R⁶ are each H or $C_1$-$C_5$-alkyl)

Dihalocarbene addition and subsequent dehalogenation are carried out in a subsequent stage (correspondingly substituted benzonitriles, benzaldehydes or benzyl alcohols), where Z, X, R¹ and R⁴-R⁶ have the above-mentioned meanings:

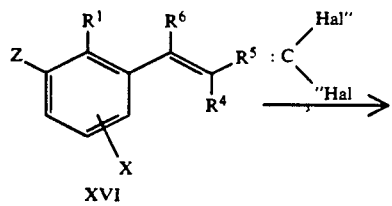

XVI

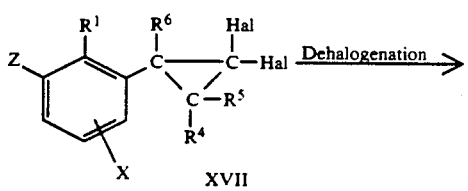

XVII

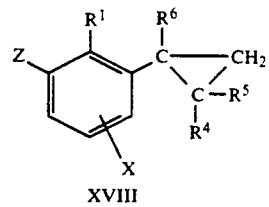

XVIII where Z is —CHO or

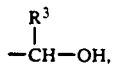

it is advantageous to introduce protective groups for these functional groups beforehand (for example acetal or tetrahydropyranyl ether) and to eliminate these in a conventional manner after the dehalogenation.

The novel compounds or their intermediates are prepared in accordance with the descriptions of the following examples or by appropriate modification of these examples.

EXAMPLE 1

Preparation of benzyl alcohols VII 1-(3'-Chloro-2'-methylphenyl)-cyclohexanol 96 g (4 moles) of Mg turnings in 60 ml of absolute tetrahydrofuran (THF) are initially taken under a nitrogen atmosphere. 1 ml of 1,2-dibromoethane is added at 65° C., after which a solution of 644 g (4 moles) of 2,6-dichlorotoluene in 1.5 l of absolute THF is added dropwise in the course of 2¼ hours. Thereafter, the mixture is stirred for 4 hours under reflux and cooled to room temperature, and 352.8 g (3.6 moles) of cyclohexanone in 250 ml of absolute THF are added under nitrogen. When the reaction is complete, the Grignard reaction mixture is worked up in an aqueous medium in a conventional manner and the solvent is substantially removed by distillation under reduced pressure. The residue is subjected to incipient distillation (30°-107° C./0.27 mbar). The remaining crude product (676 g), which contains as much as 90% of 1-(3-chloro-2'-methylphenyl)-cyclohexanol, can be further purified by column chromatography using toluene as the mobile phase.

300 MHz NMR spectrum in $CDCl_3$:
δ [ppm] = 1.58–2.0(1OH); 2.65(3H); 7.04(1H); 7.23–7.34(2H).

For example, the following alcohols, which are characterized by the physical data stated, are prepared by the process described above:

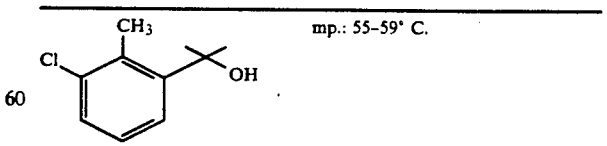

mp.: 55–59° C.

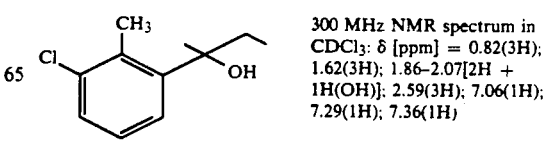

300 MHz NMR spectrum in $CDCl_3$: δ [ppm] = 0.82(3H); 1.62(3H); 1.86–2.07[2H + 1H(OH)]; 2.59(3H); 7.06(1H); 7.29(1H); 7.36(1H)

-continued

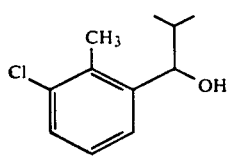
300 MHz NMR spectrum in CDCl₃: δ [ppm] = 0.84(3H); 0.96(3H); 1.83-1.96(1H); 2.19(1H); 2.32(3H); 4.63(1H); 7.1(1H); 7.23-7.33(2H)

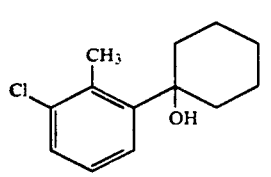
mp.: 113° C.

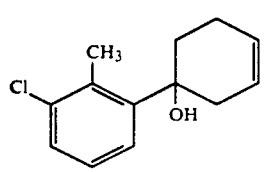
mp.: 90-93° C.

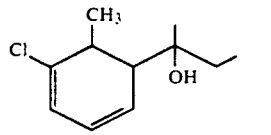
mp.: 52-55° C.

EXAMPLES 2 TO 31

Preparation of halobenzene derivatives III

2-Methyl-3-isopropenylchlorobenzene 190 g of 3-chloro-2-methyl-alpha,alpha-dimethylbenzyl alcohol are refluxed with 1.5 l of toluene and 370 g of oxalic acid under a water separator until no more water separates off. The oxalic acid is filtered off under suction and the filtrate is washed with sodium bicarbonate solution, dried over sodium sulfate and evaporated down. Fractional distillation of the residue gives 91.5 g of the desired compound, which is listed in Table 1 as Example 2.

300 MHz NMR spectrum in CDCl₃:
δ][ppm]=1.98(3H); 2.32(3H); 4.82(1H); 5.17(1H); 6.95-7.07(2H); 7.23(1H).

3-Cyclohexyl-2-methylchlorobenzene 103 g of 1-(3'-chloro-2'-methylphenyl)-cyclohexene are dissolved in 1,200 ml of ethanol, and 5 g of Pd/carbon are added. Hydrogenation is carried out for 8 hours at room temperature and under a hydrogen pressure of 80 bar. The catalyst is filtered off from the reaction mixture and the solution is evaporated down. Fractional distillation gives 51.8 g of 3-cyclohexyl-2-methylchlorobenzene (Example 3 in Table 1).

300 MHz NMR spectrum in CDCl₃:
δ [ppm]=1.2-1.49(5H); 1.7-1.92(5H); 2.36(3H); 2.72(1H); 7.01-7.2(3H).

The compounds stated in Table 1 below were prepared similarly to Example 2 or 3 described above and are characterized by the physical data stated; the other compounds in Table 1 can readily be obtained using corresponding starting materials.

TABLE 1

Halobenzene derivatives of the formula III

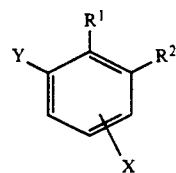

III

| Example | Y | R¹ | R² | X | Physical Data |
|---|---|---|---|---|---|
| 2 | Cl | CH₃ | Isopropenyl | H | bp. 54-55° C./0.13 mbar |
| 3 | Cl | CH₃ | Cyclohexyl | H | bp. 88-93° C./0.013 bar |
| 4 | Cl | CH₃ | n-Propyl | H | |
| 5 | Cl | CH₃ | —C(CH₃)=CH—CH₃ | H | |
| 6 | Br | CH₃ | Cyclopentyl | H | |
| 7 | Cl | CH₃ | 1-Cyclohexenyl | H | bp. 95-98° C./0.2 mbar n_D²³ = 1.5501 |
| 8 | Br | C₂H₅ | Isopropyl | H | |
| 9 | Cl | CH₃ | Cyclohexyl | 5-F | |
| 10 | Cl | CH₃ | Isopropyl | 5-Cl | |
| 11 | Cl | CH₃ | Isopropyl | H | bp. 55° C./0.27 mbar |
| 12 | Br | CH₃ | Isopropyl | H | |
| 13 | Cl | C₂H₅ | Isopropenyl | H | |
| 14 | Br | CH₃ | Isopropenyl | H | |
| 15 | Cl | CH₃ | sec-Butyl | H | bp. 58-60° C./0.13 mbar |
| 16 | Cl | CH₃ | —C(CH₃)—C(CH₃)₃ | H | |
| 17 | Cl | CH₃ | 1-Cyclopentenyl | H | |
| 18 | Cl | CH₃ | 2,5-Norbornadien-2-yl | H | |

TABLE 1-continued
Halobenzene derivatives of the formula III

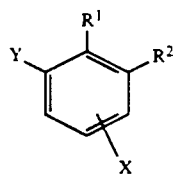

| Example | Y  | $R^1$    | $R^2$                              | X   | Physical Data |
|---------|----|----------|------------------------------------|-----|---------------|
| 19      | Cl | $CH_3$   | 2-Norbornen-2-yl                   | H   | bp. 113° C./0.06 mbar $n_D^{21} = 1.5702$ |
| 20      | Cl | $CH_3$   | 2-Norbornen-2-yl                   | 5-F | |
| 21      | Br | $CH_3$   | 2-Norbornen-2-yl                   | H   | |
| 22      | Cl | $C_2H_5$ | Norborn-2-yl                       | H   | |
| 23      | Cl | $CH_3$   | Norborn-2-yl                       | H   | bp. 109–110° C./0.013 mbar |
| 24      | Cl | $CH_3$   | 3,5-Diethylcyclohexyl              | H   | |
| 25      | Cl | $CH_3$   | 1,3-Cyclohexadienyl                | H   | |
| 26      | Br | $CH_3$   | $-\overset{C_2H_5}{\underset{\|}{C}}=CH-CH_3$ | | |
| 27      | Cl | $CH_3$   | $-\overset{C_2H_5}{\underset{\|}{C}}=CH-CH_3$ | H | bp. 70–72° C./0.013 mbar |
| 28      | Cl | $C_2H_5$ | $-\overset{C_2H_5}{\underset{\|}{C}}=CH-CH_3$ | H | |
| 29      | Cl | $CH_3$   | $-\overset{CH_2-CH_2-CH=CH_2}{\underset{\|}{C}}=CH_2$ | H | |
| 30      | Cl | $CH_3$   | $-\overset{CH_2-CH(CH_3)_2}{\underset{\|}{C}}=CH_2$ | H | |
| 31      | Cl | $CH_3$   | $-CH(C_2H_5)_2$                    | H   | bp. 60–62° C./0.013 mbar |

EXAMPLES 32 TO 65 AND 131

Preparation of benzonitriles Ic 3-(1'-cyclohexenyl)-2-methylbenzonitrile 250 g (0.6 mole) of 1-(3'-chloro-2'-methylphenyl)cyclohexene, 600 ml of 1-methyl-2-pyrrolidone and 63 g of anhydrous copper(I) cyanide are heated to the boil for 35 hours while stirring. The reaction mixture is poured into a solution of 500 ml of ethylenediamine in 1.5 l of water and the mixture is stirred for 45 minutes at 50° C. and extracted several times with toluene. The combined organic phases are extracted by shaking with 10% strength sodium cyanide solution, dried over $Na_2SO_4$ and evaporated down. Purification by column chromatography over silica gel using 3:7 toluene/cyclohexane as the eluent gives 117.8 g of the nitrile of melting point 54°–57° C.

250 MHz NMR spectrum in $CDCl_3$:

δ [ppm]=1.72(4H); 2.13(4H); 2.46(3H); 5.55(1H); 7.17–7.31(2H); 7.49(1H).

The novel benzonitriles stated in Table 2 were prepared by the process described above and are characterized by the physical properties stated; the other compounds in Table 2 can readily be obtained using corresponding starting materials.

TABLE 2
Benzonitriles of the formula Ic

| Example | $R^1$    | $R^2$          | X | Physical Properties |
|---------|----------|----------------|---|---------------------|
| 32      | $CH_3$   | 1-Cyclohexenyl | H | mp.: 54 to 57° C. |
| 33      | $CH_3$   | n-Propyl       | H | |
| 34      | $CH_3$   | n-Butyl        | H | |
| 35      | $CH_3$   | $-CH(C_2H_5)_2$ | H | $n_D^{23}$: 1.5119 |
| 36      | $C_2H_5$ | Isopropyl      | H | |
| 37      | $CH_3$   | Isopropyl      | H | 300-MHz-NMR-spectrum in $CDCl_3$: |

TABLE 2-continued

Benzonitriles of the formula Ic

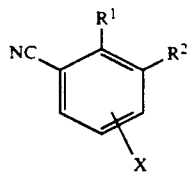

| Example | R¹ | R² | X | Physical Properties |
|---|---|---|---|---|
| | | | | δ [ppm] = 1.23(6H); 2.55(3H); 3.19(1H); 7.25(1H); 7.46(2H) |
| 38 | CH₃ | Isopropyl | 6-F | |
| 39 | CH₃ | $\underset{-C=CH_2}{C_2H_5}$ | H | |
| 40 | C₂H₅ | Isopropenyl | H | |
| 41 | CH₃ | $\underset{-C=CH-CH_3}{CH_3}$ | H | |
| 42 | CH₃ | Isopropenyl | H | 200-MHz-NMR-spectrum in CDCl₃: δ [ppm] = 2.02(3H); 2.52(3H); 4.89(1H); 5.3(1H); 7.22-7.4(2H); 7.56(1H) |
| 43 | CH₃ | Isopropenyl | 5-Cl | |
| 44 | CH₃ | $\underset{-C=C(CH_3)_2}{CH_3}$ | H | |
| 45 | CH₃ | $\underset{-C=CH_2}{i\text{-}C_3H_7}$ | H | |
| 46 | CH₃ | $\underset{-C=CH_2}{CH_2-CH_2-CH=CH_2}$ | H | |
| 47 | CH₃ | sec. Butyl | H | 200-MHz-NMR-spectrum in CDCl₃: δ [ppm] = 0.84(3H); 1.2(3H); 1.61(2H); 2.54(3H); 2.94(1H); 7.2-7.31(1H); 7.43(2H) |
| 48 | C₂H₅ | sec. Butyl | H | |
| 49 | CH₃ | $\underset{-CH-CH_3}{i\text{-}C_3H_7}$ | H | |
| 50 | C₂H₅ | CH(C₂H₅)₂ | H | |
| 51 | CH₃ | Cyclopentyl | H | |
| 52 | CH₃ | Cyclohexyl | H | 300-MHz-NMR-spectrum in CDCl₃: δ [ppm] = 1.2-1.5(5H); 1.71-1.93(5H); 2.55(3H); 2.75(1H); 7.23(1H); 7.42(2H) |
| 53 | CH₃ | Cyclopropyl | H | |
| 54 | CH₃ | 1-Cyclopentenyl | H | |
| 55 | CH₃ | 1,3-Cyclohexadienyl | H | |
| 56 | CH₃ | 2-Norbornen-2-yl | H | |
| 57 | CH₃ | Norborn-2-yl | H | mp. 74 to 76° C. |
| 58 | C₂H₅ | Cyclohexyl | H | |
| 59 | CH₃ | 2,5-Norbornadien-2-yl | H | |
| 60 | CH₃ | Cycloheptyl | H | |
| 61 | CH₃ | $\underset{-CH-CH_2-CH_2-CH_3}{CH_3}$ | H | |
| 62 | CH₃ | $\underset{-C=CH-CH_3}{C_2H_5}$ | H | $n_D^{22}$: 1.5254 |
| 63 | CH₃ | $\underset{-C=CH-CH_3}{C_2H_5}$ | 5-F | |
| 64 | C₂H₅ | $\underset{-C=CH-CH_3}{C_2H_5}$ | H | |

TABLE 2-continued

Benzonitriles of the formula Ic

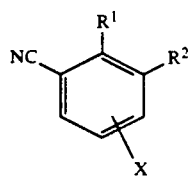

| Example | R¹ | R² | X | Physical Properties |
|---|---|---|---|---|
| 65 | $CH_3$ | $-CH(i-C_3H_7)_2$ | H | |
| 131 | $CH_3$ | $C_2H_5$<br>$\|$<br>$-C(CH_3)_2$ | H | 300-MHz-NMR-spectrum in $CDCl_3$:<br>δ [ppm] = 0.65(3H); 1.41(6H); 1.83(2H);<br>2.72(3H); 7.2(1H); 7.5(2H) |

EXAMPLES 66 TO 94 AND 132

Preparation of the benzaldehydes Ib 3-(1'-cyclohexenyl)-2-methylbenzaldehyde 460 ml (0.69 mole) of diisobutylaluminum hydride solution (25% strength solution in toluene) are carefully added dropwise at 20°-30° C. to a solution of 113 g (0.574 mole) of 3-(1'-cyclohexenyl)-2-methylbenzonitrile in 1,000 ml of dry toluene under nitrogen. The mixture is stirred for a further 4 hours at room temperature and excess diisobutylaluminum hydride is decomposed with 120 ml of methanol. 1,000 ml of 10% strength hydrochloric acid are added, after which stirring is continued overnight at room temperature. The organic phase is separated off and the aqueous phase is extracted several times with toluene. The combined organic phases are washed with water and then dried over $Na_2SO_4$. Removal of the solvent gives 109 g of the aldehyde ($n_D^{22}$: 1.5621).

300 MHz NMR spectrum in $CDCl_3$:
δ [ppm] = 1.63–1.82(4H); 2.14(4H); 2.59(3H); 2.55(1H); 7.28(2H); 7.67(1H); 10.29(1H).

The novel benzaldehydes stated in Table 3 below were prepared by the process described above and are characterized by the physical properties stated; the other compounds in Table 3 can readily be obtained using corresponding starting materials.

TABLE 3

Benzaldehydes

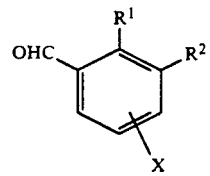

| Example | R¹ | R² | X | Physical Properties |
|---|---|---|---|---|
| 66 | $CH_3$ | 1-Cyclohexenyl | H | $n_D^{22}$ = 1.5621 |
| 67 | $CH_3$ | Cyclopentyl | H | |
| 68 | $CH_3$ | 1-Cyclopentenyl | H | |
| 69 | $C_2H_5$ | Cycloheptyl | H | |
| 70 | $CH_3$ | Cyclopropyl | H | |
| 71 | $CH_3$ | Cyclohexyl | 5-Cl | |
| 72 | $CH_3$ | Cyclohexyl | H | mp. 42–45° C. |
| 73 | $CH_3$ | Norbornen-2-yl | H | |
| 74 | $CH_3$ | 2,5-Norbornadien-2-yl | H | |
| 75 | $CH_3$ | $C_2H_5$<br>$\|$<br>$-C=CH_2$ | H | |
| 76 | $CH_3$ | $\phantom{-}\diagup CH_3$<br>$-C$<br>$\phantom{-}\diagdown CH-CH_3$ | H | |
| 77 | $CH_3$ | $-CH(C_2H_5)_2$ | H | 300-MHz-NMR-spectrum in $CDCl_3$:<br>δ [ppm] = 0.77(6H); 1.56(2H); 1.72(2H);<br>2.64(3H); 2.91(1H); 7.37(2H); 7.63(1H);<br>10.33(1H) |
| 78 | $CH_3$ | $\phantom{-}\diagup CH_3$<br>$-CH$<br>$\phantom{-}\diagdown CH_2-CH_3$ | H | 250-MHz-NMR-spectrum in $CDCl_3$:<br>δ [ppm] = 0.86(3H); 1.22(3H); 1.62(2H);<br>2.64(3H); 3.04(1H); 7.33(1H); 7.44(1H);<br>7.63(1H); 10.35(1H) |

TABLE 3-continued

Benzaldehydes

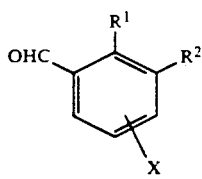
Ib

| Example | R¹ | R² | X | Physical Properties |
|---|---|---|---|---|
| 79 | C₂H₅ | −CH(CH₃)(CH₂−CH₃) | H | |
| 80 cis/trans | CH₃ | −C(=CH−CH₃)(CH₂−CH₃) | H | 200-MHz-NMR-spectrum in CDCl₃: δ [ppm] = 0.89 and 0.97(3H); 1.36 and 1.8(3H); 2.25 and 2.37(2H); 2.52 and 2.57(3H); 5.33 and 5.64(1H); 7.22–7.4(2H); 7.73(1H) |
| 81 | CH₃ | −C(=CH₂)(CH(CH₃)CH₃) | H | |
| 82 | CH₃ | −CH(CH₃)(CH(CH₃)CH₃) | H | |
| 83 | CH₃ | −C(CH₃)=C(CH₃)(CH₃) | H | |
| 84 | CH₃ | Isopropyl | H | 300-MHz-NMR-spectrum in CDCl₃: δ [ppm] = 1.27(6H); 2.66(3H); 3.3(1H); 7.33(1H); 7.5(1H); 7.65(1H); 10.32(1H) |
| 85 | CH₃ | Isopropyl | 5-F | |
| 86 | CH₃ | n-Propyl | H | |
| 87 | CH₃ | n-Butyl | H | |
| 88 | CH₃ | −CH(CH₃)(CH₂−CH₂−CH₃) | H | |
| 89 | C₂H₅ | Isopropenyl | H | |
| 90 | CH₃ | Isopropenyl | H | 200-MHz-NMR-spectrum in CDCl₃: δ [ppm] = 2.01(3H); 2.6(3H); 4.85(1H); 5.26(1H); 7.35(2H); 7.73(1H); 10.33(1H) |
| 91 | CH₃ | 1,3-Cyclohexadienyl | H | |
| 92 | CH₃ | Vinyl | H | |
| 93 | CH₃ | −CH(cyclopropyl)(CH₃) | H | |
| 94 | CH₃ | Norborn-2-yl | H | 200 MHz-NMR-spectrum in CDCl₃: δ [ppm] = 1.17–174(7H); 1.96(1H); 2.39(2H); 2.68(3H); 3.53(1H); 7.37(1H); 7.52(1H); 7.69(1H); 10.38(1H) |
| 132 | CH₃ | −C(CH₃)₂(C₂H₅) | H | 300-MHz-NMR-spectrum in CDCl₃: δ [ppm] = 0.68(3H); 1.42(6H); 1.86(2H); 2.8(3H); 7.27(1H); 7.57(1H) 7.66(1H); 10.38(1H) |

EXAMPLES 95 TO 130

Preparation of the benzyl alcohols Ia 3-(1'-cyclohexenyl)-2-methylbenzyl alcohol A solution of 24 g (0.12 mole) of 3-(1'-cyclohexenyl)-2-methylbenzaldehyde in 120 ml of ethanol is added dropwise to a suspension of 2.3 g (0.06 mole) of sodium borohydride in 120 ml of ethanol at room temperature. The mixture is stirred for 15 hours at room temperature, after which 320 ml of 5% strength hydrochloric acid are carefully added and extraction is carried out several times with ether. The combined ether phases are washed with 5% strength hydrochloric acid and then with water, dried and evaporated down. 23 g of 3-(1'-cyclohexenyl)-2-methylbenzyl alcohol of melting point 62°–64° C. (Example 95) are obtained. 3-Sec-butyl-2-methyl-alpha-ethynylbenzyl alcohol 50 ml of THF (absolute) are saturated with acetylene at 0° C. and under a nitrogen atmosphere. 87 ml of methylmagnesium chloride solution (1.5 molar) are added dropwise in the course of 45 minutes with further introduction of acetylene, and the mixture is stirred for 30 minutes at 0° C. At −20° C., a solution of 15.3 g of 3-sec-butyl-2-methylbenzaldehyde in 20 ml of THF (absolute) is added dropwise. Stirring is continued for 2 hours at −20° C., and the reaction mixture is allowed to stand overnight at room temperature and is poured into 300 ml of ice water. It is acidified with dilute hydrochloric acid and then extracted three times by shaking with ether. The combined ether extracts are washed with water, dried over sodium sulfate and evaporated down to give 16.6 g of an oil (70% of desired compound) which, after purification by column chromatography over silica gel using toluene as the mobile phase, gives 5.1 g of the pure benzyl alcohol (Example 96).

300 MHz NMR spectrum in $CDCl_3$:

$\delta$ [ppm]=0.84 (3H); 1.17(3H); 1.57(2H); 2.36(3H); 2.57(1H); 2.62(1H); 2.97(1H); 5.62(1H); 7.18(2H); 7.52(1H).

3-Cyclopropyl-2-methylbenzyl alcohol a) Dihalocarbene addition: 10 ml of methylene chloride, 0.42 ml of ethanol, 0.14 g of benzyltriethylammonium chloride and 20.9 g (0.083 mole) of bromoform are added to 9.9 g (0.042 mole) of 2-methyl-3-vinylbenzyl tetrahydro-2-pyranyl ether. After the addition of 13.28 g (0.166 mole) of ice-cold 50% strength NaOH, thorough stirring is carried out for 1 hour at room temperature and for 8 hours at 50° C. The reaction mixture is poured into 300 ml of water and is extracted three times with methylene chloride. The combined extracts are dried and evaporated down. Purification by column chromatography over silica gel using toluene as the mobile phase gives 9.1 g of 3-(2',2'-dibromocyclopropyl)-2-methylbenzyl tetrahydro-2-pyranyl ether.

250 MHz NMR spectrum in $CDCl_3$:

$\delta$ [ppm]=1.45–1.95(6H); 2.02(1H); 2.15(1H); 2.46(3H); 2.84(1H); 3.55(1H); 3.9(1H); 4.55(1H); 4.72(1H); 4.88(1H); 6.93(1H); 7.14(1H); 7.37(1H).

b) Dehalogenation: 45.2 g (0.155 mole) of tri-n-butyltin hydride are added, at 0° C., to 29.7 g (0.074 mole) of the dibromocyclopropyl compound prepared under a) and 150 ml of n-hexane. The mixture is stirred for 1 hour at room temperature and for 10 hours under reflux. It is refluxed for a further 20 hours, a total of 15 g of tri-n-butyltin hydride being added a little at a time. The cooled reaction solution is evaporated down. Purification by column chromatography over silica gel using toluene as the mobile phase gives 17.1 g of 3-cyclopropyl-2-methylbenzyl tetrahydro-2-pyranyl ether.

200 MHz NMR spectrum in $CDCl_3$:

$\delta$ [ppm]=0.62(2H); 0.91(2H); 1.5–2.0(6H+1H); 1.94(3H); 3.6(1H); 3.97(1H); 4.52(1H); 4.76(1H); 4.87(1H); 7.02.7.21(2H); 7.29(1H).

c) Elimination of the protective group: 16.7 g of 3-cyclopropyl-2-methylbenzyl tetrahydro-2-pyranyl ether in 180 ml of methanol are stirred overnight at room temperature with 10.8 ml of concentrated hydrochloric acid. The mixture is neutralized with sodium methylate solution while cooling with ice and is then evaporated down. Water is added to the residue, which is then extracted several times with ether. The combined ether extracts are washed with water, dried and evaporated down. The crude product (11.5 g) is purified by column chromatography over silica gel using toluene as the mobile phase. 8.9 g of 3-cyclopropyl-2-methylbenzyl alcohol (Example 100) are obtained.

300 MHz NMR spectrum in $CDCl_3$:

$\delta$ [ppm]0.61(2H); 0.93(2H); 1.88(1H); 2.15(1H); 2.43(3H); 4.63(2H); 6.97–7.19(3H).

The novel benzyl alcohols stated in Table 4 below were prepared by the processes described in Preparation Examples 95, 96 and 100 and are characterized by the physical properties stated; the other compounds in Table 4 can readily be obtained using corresponding starting materials.

TABLE 4

Benzyl alcohols of the formula Ia

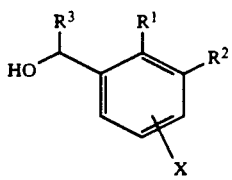

Ia

| Example | $R^1$ | $R^2$ | $R^3$ | X | Physical properties |
|---|---|---|---|---|---|
| 95 | $CH_3$ | 1-Cyclohexenyl | H | H | mp. 62 to 64° C. |
| 96 | $CH_3$ | sec-Butyl | Ethynnyl | H | 300-MHz-NMR-spectrum in $CDCl_3$: $\delta$ [ppm] = 0.84(3H); 1.17(3H); 1.57(2H); 2.36(3H); 2.57(1H); 2.62(1H); 2.97(1H); 5.62(1H); 7.18(2H); 7.52(1H) |
| 97 | $CH_3$ | Cyclopentyl | H | H | |
| 98 | $CH_3$ | 1-Cyclopentenyl | H | H | |
| 99 | $CH_3$ | 1-Cyclopentenyl | Ethynyl | H | |
| 100 | $CH_3$ | Cyclopropyl | H | H | 300-MHz-NMR-spectrum in $CDCl_3$: |

TABLE 4-continued

Benzyl alcohols of the formula Ia

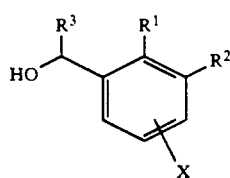

Ia

| Example | R$^1$ | R$^2$ | R$^3$ | X | Physical properties |
|---|---|---|---|---|---|
| | | | | | δ [ppm] = 0.61(2H); 0.93(2H); 1.88(1H); 2.15(1H); 2.4(3H); 4.63(2H); 6.97–7.19(3H) |
| 101 | CH$_3$ | Cyclohexyl | H | 5-Cl | |
| 102 | CH$_3$ | Cyclohexyl | H | H | mp. 87–88° C. |
| 103 | CH$_3$ | Cyclohexyl | Ethyl | H | |
| 104 | CH$_3$ | 2-Norbornen-2-yl | H | H | |
| 105 | CH$_3$ | 2,5-Norborna-dien-2-yl | H | H | |
| 106 | CH$_3$ | Norborn-2-yl | H | H | 200 MHz-NMR-spectrum in CDCl$_3$: δ [ppm] = 1.21–1.73 [7H + 1H(OH)]; 1.94(1H); 2.37(3H + 2H); 3.5(1H); 4.77(2H); 7.26(3H) |
| 107 | CH$_3$ | —CH(C$_2$H$_5$)$_2$ | H | H | 200-MHz-NMR-spectrum in CDCl$_3$: δ [ppm] = 0.79(6H); 1.49–1.8(4H); 1.7(1H); 2.34(3H); 2.85(1H); 4.74(2H); 7.21(3H); |
| 108 | CH$_3$ | Isopropyl | H | H | 300-MHz-NMR-spectrum in CDCl$_3$: δ [ppm] = 1.22(6H); 2.24(1H); 2.31(3H); 3.22(1H); 4.63(2H); 7.12–7.24(3H) |
| 109 | CH$_3$ | Isopropyl | CH$_3$ | H | 300-MHz-NMR-spectrum in CDCl$_3$: δ [ppm] = 1.22(6H); 1.43(3H); 2.27(3H); 2.45(1H); 3.21(1H); 5.14(1H); 7.19(2H); 7.35(1H); |
| 110 | CH$_3$ | Isopropyl | H | 5-Cl | |
| 111 | CH$_3$ | Isopropyl | Ethynyl | H | |
| 112 | CH$_3$ | —CH—CH(CH$_3$)$_2$ with CH$_3$ substituent | H | H | |
| 113 | CH$_3$ | n-Propyl | H | H | |
| 114 | CH$_3$ | n-Butyl | H | H | |
| 115 | CH$_3$ | Isopropenyl | H | H | 200-MHz-NMR-spectrum in CDCl$_3$: δ [ppm] = 1.83(1H); 2.0(3H); 2.28(3H); 4.71(2H); 4.82(1H); 5.2(1H); 7.05–7.33(3H) |
| 116 | CH$_3$ | Isopropenyl | Ethynyl | H | |
| 117 | CH$_3$ | Isopropenyl | CN | H | |
| 118 | CH$_3$ | Isopropenyl | Vinyl | H | 200-MHz-NMR-spectrum in CDCl$_3$: δ [ppm] = 2.02(3H); 2.13(broad, 1H); 2.33(3H); 4.85(1H); 5.19–5.5(4H); 5.97–6.14(1H); 7.07(1H); 7.2(1H); 7.4(1H) |
| 119 | CH$_3$ | —C(C$_2$H$_5$)=CH$_2$ | H | H | |
| 120 | CH$_3$ | —C(CH$_3$)=CH—CH$_3$ | H | H | |
| 121 | CH$_3$ | —C(C$_2$H$_5$)=CH—CH$_3$ | H | H | n$_D^{22}$: 1.5325 |
| 122 | CH$_3$ | —CH(CH$_3$)—CH$_2$—CH$_3$ | H | H | 200-MHz-NMR-spectrum in CDCl$_3$: δ [ppm] = 0.88(3H); 1.22(3H); 1.64(2H); 1.86(1H); 2.33(3H); 3.0(1H); 4.72(2H); 7.22(3H) |
| 123 | CH$_3$ | —CH(C$_2$H$_5$)$_2$ | Isopropyl | H | |
| 124 | C$_2$H$_5$ | —CH(CH$_3$)—CH$_2$—CH$_3$ | H | H | |
| 125 | CH$_3$ | —C(CH$_3$)=C(CH$_3$)$_2$ | H | H | |
| 126 | CH$_3$ | —C(i-C$_3$H$_7$)=CH$_2$ | H | H | |
| 127 | CH$_3$ | 3,5-Diethyl- | H | H | |

TABLE 4-continued
Benzyl alcohols of the formula Ia

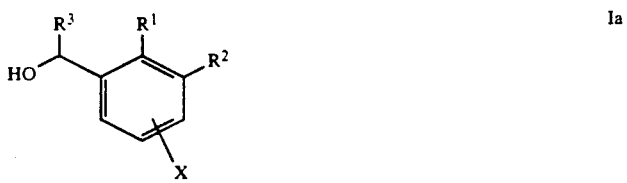

| Example | R¹ | R² | R³ | X | Physical properties |
|---|---|---|---|---|---|
| | | cyclohexyl | | | |
| 128 | $CH_3$ | $\underset{-\overset{\mid}{C}=CH_2}{CH_2-CH_2-CH=CH_2}$ | H | H | |
| 129 | $CH_3$ | vinyl | H | H | 300-MHz-NMR-spectrum in $CDCl_3$: $\delta$ [ppm] = 1.97(1H); 2.29(3H); 4.65(2H); 5.3(1H); 5.58(1H); 6.93–7.04(1H); 7.11–7.28(2H); 7.4(1H) Schmp: 38–43° C. |
| 130 | $CH_3$ | $\underset{-\overset{\mid}{C}-(CH_3)_2}{C_2H_5}$ | H | H | 300-MHz-NMR-spectrum in $CDCl_3$: $\delta$ [ppm] = 0.67(3H); 1.39(6H); 1.83(2H + 1H); 2.46(3H); 4.66(2H); 7.09–7.31(3H) |

We claim:

1. A novel benzonitrile of formula I:

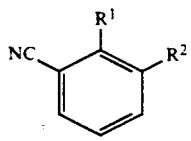

wherein R¹ is methyl or ethyl, and R² is a member selected from the group consisting of branched $C_{3-20}$ alkyl and branched $C_{3-20}$ alkenyl.

2. A novel benzonitrile of the formula I:

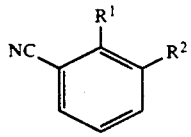

wherein R¹ is methyl or ethyl, and R² is $C_{3-8}$ cycloalkyl, $C_{3-8}$ cycloalkenyl, $C_{5-12}$ bicycloalkyl, $C_{5-12}$ bicycloalkenyl, $C_1$-$C_5$-alkyl-substituted $C_{3-8}$ cycloalkyl, $C_{1-5}$-alkyl-substituted, $C_{3-8}$ cycloalkenyl, $C_{1-5}$-alkyl-substituted, $C_{5-12}$ bicycloalkyl $C_1$-$C_5$-alkyl-substituted and $C_{5-12}$ bicycloalkenyl.

3. The compound of claim 1, wherein R¹ is methyl.
4. The compound of claim 1, wherein R¹ is ethyl.
5. The compound of claim 1, wherein R² is branched $C_{3-20}$ alkyl.
6. The compound of claim 1, wherein R² is branched $C_{3-20}$ alkenyl.
7. The compound of claim 2, wherein R² is $C_{3-8}$ cycloalkyl.
8. The compound of claim 2, wherein R² is $C_{3-8}$ cycloalkenyl.
9. The compound of claim 1, wherein R² is $C_{5-12}$ bicycloalkyl.
10. The compound of claim 1, wherein R² is $C_{5-12}$ bicycloalkenyl.
11. The compound of claim 1, wherein R² is $C_1$-$C_5$-alkyl-substituted $C_{5-12}$ cycloalkyl.
12. The compound of claim 1, wherein R² is $C_1$-$C_5$-alkyl-substituted $C_{5-12}$ cycloalkenyl.
13. The compound of claim 1, wherein R² is $C_1$-$C_5$-alkyl-substituted $C_{5-12}$ bicycloalkyl.
14. The compound of claim 1, wherein R² is $C_1$-$C_5$-alkyl-substituted $C_{5-12}$ bicycloalkenyl.

* * * * *